United States Patent
Lacroix

(10) Patent No.: US 10,095,830 B2
(45) Date of Patent: Oct. 9, 2018

(54) SPRAY NOZZLE FOR FLUIDIZED CATALYTIC CRACKING

(71) Applicant: Spraying Systems Co., Wheaton, IL (US)

(72) Inventor: Mark Lacroix, Thornton, NH (US)

(73) Assignee: Spraying Systems Co., Wheaton, IL (US)

( * ) Notice: Subject to any disclaimer, the term of this patent is extended or adjusted under 35 U.S.C. 154(b) by 101 days.

(21) Appl. No.: 15/023,473

(22) PCT Filed: Sep. 18, 2014

(86) PCT No.: PCT/US2014/056334
§ 371 (c)(1),
(2) Date: Mar. 21, 2016

(87) PCT Pub. No.: WO2015/042276
PCT Pub. Date: Mar. 26, 2015

(65) Prior Publication Data
US 2016/0214074 A1    Jul. 28, 2016

Related U.S. Application Data

(60) Provisional application No. 61/880,268, filed on Sep. 20, 2013.

(51) Int. Cl.
*B01J 4/00* (2006.01)
*G06F 19/22* (2011.01)
(Continued)

(52) U.S. Cl.
CPC .............. *G06F 19/22* (2013.01); *B01J 4/002* (2013.01); *B01J 8/1827* (2013.01); *B01J 8/24* (2013.01);
(Continued)

(58) Field of Classification Search
CPC ................... B01J 8/1818; B01J 8/1845; B01J 2208/00902; B01J 8/22; B01J 4/002;
(Continued)

(56) References Cited

U.S. PATENT DOCUMENTS 2,527,093 A    10/1950   Du Fay
4,349,456 A    9/1982    Haruch et al.
(Continued)

FOREIGN PATENT DOCUMENTS

CN    101495239 A    7/2009
EP    1312417 A2    5/2003
(Continued)

OTHER PUBLICATIONS

First Office Action dated Jun. 27, 2017, in Chinese Patent Application No. 201480063339.4.
(Continued)

*Primary Examiner* — Steven J Ganey
*Assistant Examiner* — Juan C Barrera
(74) *Attorney, Agent, or Firm* — Leydig, Voit & Mayer, Ltd.

(57) ABSTRACT

A gas assisted spray nozzle assembly having a nozzle body in the form of a one piece hollow tubular member, such as a single cylindrical pipe section, which defines a mixing zone and a downstream barrel extension zone. A liquid inlet and an impingement pin are supported by said tubular member in opposed relation to each other at the mixing zone, and pressurized gas inlet is provided at an upstream end of the tubular member. The impingement pin in this case has an impingement surface radially offset from a central axis of the mixing zone on a side opposite the liquid inlet for receiving pressurized liquid and redirecting the liquid toward the central axis for enhanced intermixing with and atomization by the pressurized gas stream.

6 Claims, 2 Drawing Sheets

(51) Int. Cl.
  *B01J 8/18* (2006.01)
  *C10G 11/18* (2006.01)
  *G06F 19/24* (2011.01)
  *B01J 8/24* (2006.01)
  *B05B 7/04* (2006.01)

(52) U.S. Cl.
  CPC ............ *B05B 7/0416* (2013.01); *C10G 11/18* (2013.01); *G06F 19/24* (2013.01); *B01J 2208/00902* (2013.01)

(58) Field of Classification Search
  CPC ......... B01J 8/1827; B01J 8/24; B05B 7/0466; B05B 7/0458; B05B 7/0475; C10G 11/18; G06F 19/22; G06F 19/24
  USPC ..... 239/418, 424, 424.5, 426, 481, 432, 434
  See application file for complete search history.

(56) References Cited

U.S. PATENT DOCUMENTS

| | | | |
|---|---|---|---|
| 4,565,324 A | 1/1986 | Rebula et al. | |
| 4,591,099 A * | 5/1986 | Emory | B05B 1/042 239/419 |
| 4,815,665 A | 3/1989 | Haruch | |
| 4,989,788 A * | 2/1991 | Bendig | B05B 1/042 239/429 |
| 5,176,325 A * | 1/1993 | Vidusek | B05B 7/0483 239/419.3 |
| 5,372,312 A * | 12/1994 | Vidusek | B05B 1/14 239/104 |
| 5,603,453 A * | 2/1997 | Weaver | B05B 7/0075 239/419.3 |
| 5,732,685 A | 3/1998 | Nakamura | |
| 5,921,472 A * | 7/1999 | Haruch | B01J 8/1827 239/432 |
| 6,098,896 A | 8/2000 | Haruch | |
| 6,726,127 B2 * | 4/2004 | Hofherr | B05B 1/042 239/432 |
| 7,611,080 B2 * | 11/2009 | Peterson | B05B 1/3415 239/463 |
| 2006/0038041 A1 | 2/2006 | Huffman et al. | |

FOREIGN PATENT DOCUMENTS

| | | |
|---|---|---|
| WO | WO 2015/042278 A1 | 3/2015 |
| WO | WO 2015/073133 A1 | 5/2015 |

OTHER PUBLICATIONS

European Search Report dated Feb. 28, 2017, in European Patent Application No. 14845507.4.
International Search Report dated Dec. 31, 2014, in International Application No. PCT/US2014/056334.

* cited by examiner

SPRAY NOZZLE FOR FLUIDIZED CATALYTIC CRACKING

CROSS-REFERENCE TO RELATED APPLICATIONS

This patent application claims the benefit of U.S. Patent Application No. 61/880,268, filed Sep. 20, 2013, which is incorporated by reference.

FIELD OF THE INVENTION

The present invention relates generally to spray nozzles, and more particularly, to spray nozzle assemblies particularly adapted for atomizing and spraying a liquid feed to a fluidized catalytic cracking riser reactor.

BACKGROUND OF THE INVENTION

A spray nozzle assembly of the foregoing type is shown and described in U.S. Pat. No. 5,921,472, the disclosure of which is incorporated by reference. Such spray nozzle assemblies typically include a nozzle body which defines a mixing chamber into which a liquid hydrocarbon and pressurized gas, such as steam, are introduced and within which the liquid hydrocarbon is atomized. To enhance liquid atomization within the mixing chamber, an impingement pin extends into the chamber and defines a liquid impingement surface on the center line of the mixing chamber in diametrically opposed relation to the liquid inlet against which a pressurized liquid stream impinges and is transversely dispersed and across which pressurized steam from a gas inlet is directed for further interaction and shearing of the liquid into fine droplets. The atomized liquid within the mixing chamber is directed under the force of the pressurized steam through an elongated tubular barrel, commonly disposed within a wall of the catalytic reactor riser, for discharge from a spray tip at a downstream end thereof within the riser.

The nozzle body, which defines the mixing chamber and receives the impingement pin, a liquid hydrocarbon inlet, and a pressurized steam inlet, is a relatively expensive component of the spray nozzle assembly. The nozzle body commonly is machined from solid metal stock, which due to its complexity, is laborious and time consuming, substantially increasing the cost of the nozzle assembly. Moreover, since the end of the impingement pin is disposed within the path of travel of the pressurized stream, it further is susceptible to erosion from the steam injection, causing the necessity for periodic costly replacement. For effective operation, it further is required that the atomized liquid hydrocarbon and steam continue to intermix during travel through the elongated barrel of the nozzle assembly without undesirable stratification.

SUMMARY AND OBJECTS OF THE INVENTION

It is an object of the invention to provide a liquid hydrocarbon feed spray nozzle assembly that is relatively simple in construction and lends itself to significantly more economical manufacture.

Another object is to provide a spray nozzle assembly as characterized above that is effective for efficiently atomizing and spraying liquid hydrocarbons in catalytic cracking systems with less susceptibility to wear and erosion during long term usage.

Other objects and advantages of the invention will become apparent upon reading the following detailed description and upon reference to the drawings, in which:

Figure 1:
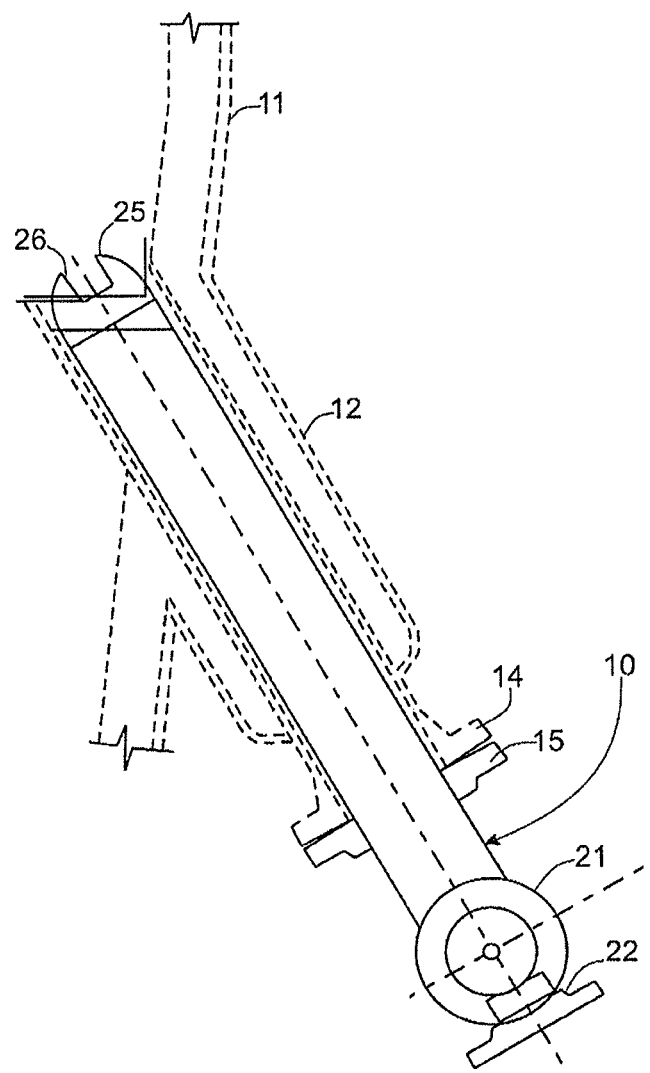
FIG. 1 is a schematic depiction of a spray nozzle assembly in accordance with the present invention mounted within the wall of a riser of a catalytic cracking reactor.

While the invention is susceptible of various modifications and alternative constructions, a certain illustrative embodiment thereof has been shown in the drawings and will be described below in detail. It should be understood, however, that there is no intention to limit the invention to the specific form disclosed, but on the contrary, the intention is to cover all modifications, alternative constructions, and equivalents falling within the spirit and scope of the invention. In that regard, while the illustrated spray nozzle assembly is particularly effective for atomizing and spraying liquid hydrocarbons in catalytic cracking systems, it will be understood that the utility of the nozzle assembly is not limited to that usage.

DESCRIPTION OF THE PREFERRED EMBODIMENT

Referring now more particularly to the drawings there is shown an illustrative spray nozzle assembly 10 in accordance with the invention mounted in a conventional manner in an insulated wall 11 (shown in phantom) of a riser of a fluidized catalytic reactor. The spray nozzle assembly 10 is supported in a tubular sleeve 12 fixed within the wall 11 at an acute angle to the vertical for discharging atomized liquid hydrocarbon upwardly into the riser. The tubular sleeve 12 has an outwardly extending flange 14 to which a support flange 15 fixed to the spray nozzle assembly 10 may be secured.

Figure 2:
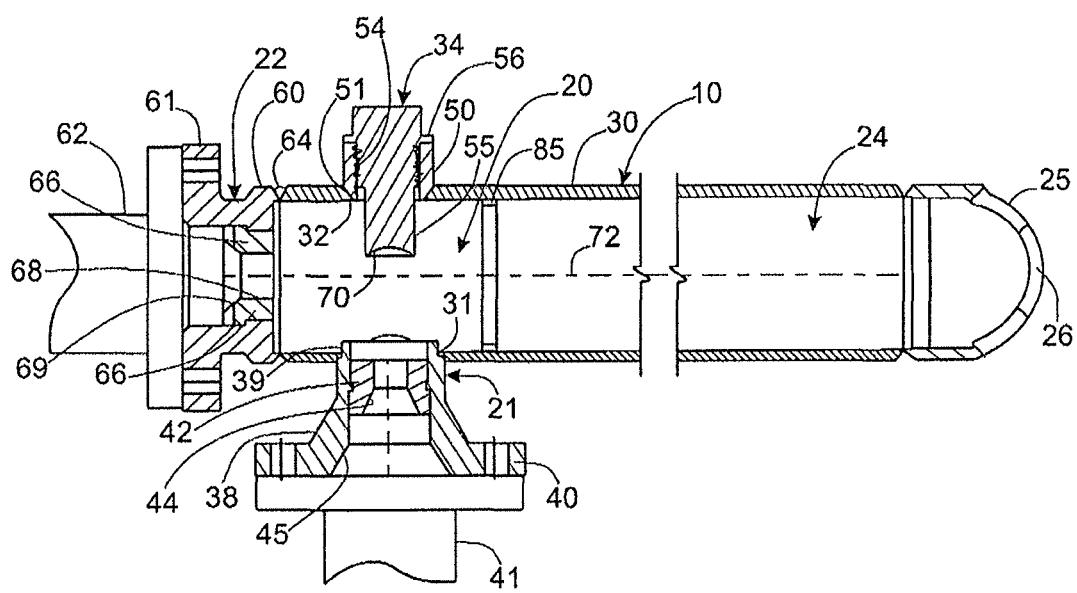
FIG. 2 is an enlarged longitudinal section of the spray nozzle assembly shown in FIG. 1.

The spray nozzle assembly 10, as best depicted in FIG. 2, basically comprises a mixing zone 20 having a liquid hydrocarbon inlet 21 and a pressurized steam or gas inlet 22 disposed on an outer side of the wall 11 of the riser, an elongated barrel extension zone 24 communicating with the mixing zone 20 and extending through the nozzle support sleeve 12 and riser wall 11, and a spray tip 25 having one or more discharge orifices 26 disposed within the riser for discharging and directing the atomized liquid spray.

In accordance with the invention, the spray nozzle assembly has a relatively simple construction that lends itself to economical manufacture, while being operable for effecting efficient atomization and direction of liquid hydrocarbon feeds in catalytic cracking systems. To this end, in the illustrated embodiment, the mixing zone 20 and barrel zone 24 are defined by a common nozzle body in the form of an uninterrupted cylindrical tubular member 30 which extends substantially the length of the spray nozzle assembly. The tubular member 30 may be a single one piece length of pipe, such as Schedule 80 steel pipe, having an internal diameter of about 2 to 8 inches. The tubular member 30 in this instance has diametrically opposed drilled openings 31, 32 adjacent an upstream end for receiving the liquid inlet 21 and an opposed impingement pin 34, respectively.

The illustrated liquid inlet 21 includes an inlet fitting 38 having a reduced diameter counter bore section 39 that fits within the opening 31, which in this case is formed with an inwardly tapered conical sidewall for facilitating securement of the fitting 38 to the tubular member 30 by an appropriate annular weldment. The liquid inlet fitting 38 has an upstream mounting flange 40 for securement of the fitting 38 to a supply line 41 which in turn is coupled to a suitable liquid hydrocarbon supply. The liquid inlet fitting 38 receives an internally mounted orifice member 42 which defines a liquid inlet flow passage 44 of predetermined diameter through which the feed liquid is directed into the mixing zone 20. The illustrated orifice member 42 and fitting 38, have respective conical entry sections 44, 45 for channeling the feed liquid into and through the orifice member 42.

The impingement pin 34 in this case is in the form of a threaded bolt mounted within an internally threaded bushing or threadolet 50 having an inwardly chamfered end 51 adjacent an inwardly chamfered side of the opening 32 for facilitating welding of the bushing 50 about the opening 32. The impingement pin 34 in this instance has an externally threaded outer section 54 for adjustable threaded engagement with the bushing 50, an inwardly extending cylindrical post section 55 disposed within the tubular member 30, and a head having an outwardly extending flange 56 for fixing the post section 55 in predetermined position within the mixing zone 20 in opposed relation to the liquid inlet 21.

The steam inlet 22, like the liquid inlet 21, includes a fitting 60 having a mounting flange 61 for securement to a supply line 62 coupled to a steam or other pressurized gas or air supply and a downstream cylindrical section for securement to an upstream axial end of the tubular member 30. The ends of the steam inlet fitting 60 and the tubular member 30 again are chamfered for facilitating securement by a weldment 64. The steam inlet fitting 60 includes an orifice member 66 for defining a steam inlet passage 68 of predetermined diameter for the pressurized steam with an upstream conical section 69 for channeling steam into and through the inlet passage 68.

In accordance with a further feature of this embodiment, the impingement pin 34 is designed for enhancing liquid breakup and atomization by the pressurized steam cross flow with lesser susceptibility to wear and erosion of the impingement pin. To this end, the impingent surface of the pin 34 has an outer impingement surface 70 disposed in radially offset relation to a central axis of the mixing zone 20 on a side of the center line opposite the liquid inlet 21 and has an inwardly recessed configuration for redirecting liquid impinging upon the impingement surface 70 back into the center of the mixing zone for enhanced interaction with the cross flow of pressurized stream for the steam inlet 22. The recessed impingement surface 70 in this case has an inwardly curved spherical configuration. Alternatively, the inward recess of the impingement surface may have a cylindrical configuration with an axis of the cylindrical surface preferably disposed transversely to the central axis 72 of the tubular member 30. In the preferred embodiment, the impingement surface 70 is set back a distance "d" from the central axis of the mixing zone of between $\frac{1}{8}$ and $\frac{1}{3}$ the radius of the mixing chamber, and most preferably about $\frac{1}{4}$ the radius of the mixing zone.

Hence, during operation of the spray nozzle assembly 10, liquid hydrocarbon directed into the mixing zone 20 will pass through the cross flow of pressurized steam directed into the spray nozzle assembly from the steam inlet 22 and engage the recessed impingement surface 70 of the impingement pin 34, which shatters the liquid, disperses it transversely, and redirects it back into the center of the mixing zone 20 for further enhanced liquid particle breakdown and direction under the force of the steam into and through the barrel extension zone 24. With the recessed impingement face 70 in radially removed relation to the axis 72 of the mixing zone 20, the pressurized cross flow of steam enhances liquid particle breakdown with lesser impediment from the impingement pin to the axial flow of steam through the mixing zone and into the barrel zone. The radial spacing of the impingement surface 70 with respect to the central axis 72 of the mixing zone 20 further minimizes the direct impact of the stream on the end of the impingement pin 34 and resulting erosion about the impingement surface 70 which can adversely affected spray performance and cause the need for replacement of the impingement pin.

For enhancing continued intermixing of the atomized liquid and steam during its passage through the barrel extension zone 24 to the spray tip 25, an annular dispersion ring 85 in fixedly disposed between the mixing zone 20 and the barrel zone 24. The cylindrical dispersion ring 85 in this case effectively defines the downstream end of the mixing zone 20 and the upstream end of the barrel extension zone 24. Typically the barrel extension zone 24 has an axial length of 2 to 10 times the axial length of the mixing zone 20. In this case, the annular dispersion ring 85 is positioned an axial distance "1" downstream of the center of the impingement pin 34 less than the diameter of the mixing zone 20, and preferably a distance corresponding to about $\frac{3}{4}$ of the diameter of the mixing zone 20.

The illustrated dispersion ring 85 is a separate metal cylindrical ring having a relatively small radial depth that is welded or otherwise fixed within the tubular member 30. The dispersion ring 85 has a radial depth "x" less than $\frac{1}{8}$ the internal diameter of the mixing zone, and preferably about $\frac{1}{10}$ the internal diameter of the pipe that defines the mixing zone. It has unexpectedly been found that the small annular ledge or lip defined by the dispersion ring 85 will direct the peripheral portion of the axial flow of steam and atomized liquid droplets inwardly sufficient to facilitate continued intermixing of the droplets and steam as they proceed the length of the barrel zone 24 and discharge from the spray tip 25. Yet, the small radial depth "x" of the dispersion ring 85 does not undesirably impede the flow of atomized liquid from the mixing zone 20 to the barrel extension zone 24.

From the foregoing, it can be seen that a spray nozzle assembly is provided that is relatively simple in construction and lends itself economical manufacture. Yet the spray nozzle assembly is effective for efficiently atomizing and spraying liquid hydrocarbons in catalytic cracking systems with less susceptibility to wear and erosion during long term usage.

The invention claimed is:

1. A gas assisted spray nozzle assembly comprising: a nozzle body having a mixing zone and a barrel extension zone downstream of the mixing zone longer in axial length than the mixing zone; a liquid inlet supported by said nozzle body through which a liquid stream is directed into said mixing zone; an impingement pin supported by said nozzle body and extending into said mixing zone having an outer impingement surface in substantial alignment with the liquid inlet against which a liquid stream directed into said mixing zone from said liquid inlet impinges; a pressurized gas inlet mounted in an upstream end of said nozzle body through which a pressurized gas stream is directed into said mixing zone along a central axis of said mixing zone for atomizing liquid impinging upon said impingement surface; said impingement surface of said impingement pin being disposed in radially offset relation to the central axis of the mixing zone on a side opposite the liquid inlet a distance of between $\frac{1}{8}$ and $\frac{1}{3}$ of the radius of said mixing zone, and said impingement surface being formed with an inwardly directed recess for receiving the liquid stream introduced into said mixing zone from said liquid inlet and directing the liquid away from the impingement surface and toward the central axis of said mixing zone for intermixing with the pressurized gas stream introduced into said mixing zone from said gas inlet for enhanced break down and atomization of the liquid for direction to and through said barrel extension zone; and a spray tip mounted at a downstream end of said nozzle body having a discharge orifice through which said atomized liquid is discharged in a predetermined spray pattern.

2. The spray nozzle assembly of claim 1 in which said nozzle body is a tubular member formed with a first opening adjacent an upstream end thereof that receives said liquid inlet and a second opening in opposed relation to the said first opening for receiving said impingement pin.

3. The spray nozzle assembly of claim 2 in which said tubular member is a one piece pipe section.

4. The spray nozzle assembly of claim 2 in which said recess in said impingement surface has an inwardly curved configuration.

5. The spray nozzle assembly of claim 4 in which said recess in said impingement surface has a spherical configuration.

6. The spray nozzle assembly of claim 4 in which said recess in said impingement surface has a cylindrical configuration.

\* \* \* \* \*